(12) United States Patent
Wong et al.

(10) Patent No.: US 6,260,021 B1
(45) Date of Patent: Jul. 10, 2001

(54) COMPUTER-BASED MEDICAL IMAGE DISTRIBUTION SYSTEM AND METHOD

(75) Inventors: Stephen Wong, San Francisco; Fred Prior, Belmont, both of CA (US)

(73) Assignee: Philips Electronics North America Corporation, New York, NY (US)

( * ) Notice: Subject to any disclaimer, the term of this patent is extended or adjusted under 35 U.S.C. 154(b) by 0 days.

(21) Appl. No.: 09/096,694

(22) Filed: Jun. 12, 1998

(51) Int. Cl.[7] .................................................. G06F 17/60
(52) U.S. Cl. ...................... 705/2; 705/3; 705/1; 709/303; 707/103
(58) Field of Search ....................... 705/3, 2, 1; 709/303; 707/103

(56) References Cited

U.S. PATENT DOCUMENTS

| | | | |
|---|---|---|---|
| 5,581,460 | * 12/1996 | Kotake et al. | 705/3 |
| 5,586,262 | * 12/1996 | Komatsu et al. | 705/2 |
| 5,655,084 | * 8/1997 | Pinsky et al. | 705/3 |
| 5,671,353 | * 9/1997 | Tian et al. | 714/48 |
| 5,740,428 | * 4/1998 | Mortimore et al. | 707/104 |
| 5,835,735 | * 11/1998 | Mason et al. | 710/107 |
| 5,838,970 | * 11/1998 | Thomas | 709/303 |

OTHER PUBLICATIONS von Land et al., "Object–Oriented Design of the DICOM Standard and its Application to Cardiovascular Imaging," Computers in Cardiology, vol. 24, 1997.*
Zhang et al., "Class Library Design for DICOM in C++", Engineering in Medicine and Biology Society, IEEE 17th Annual Conference, vol. 1, pp. 435–436, 1997.*
Prior FW, Glicksman R, de Greef B. Wong STC. "Computerized Patient Record (CPR) architecture based on distributed objects and Web technologies" in Proc. Healthcare Information Management Systems Society (HIMSS) 1998, vol. 2, pp. 30–38.
Moshteghi M, de Greef B, Hein H, Wang J. Wong STC, Yu PY. "Personalized Web Presentation of Computer–based Patient Records" in Proc. Healthcare Information Management Systems Society (HIMSS) 1998, vol. 4, Orlando, pp. 11–24.
Wong STC, Yu PY, Tjandra D, Glicksman R, Hamel L, Kane B, Prior FW, Carman C. "Report on performance and clinical experience of a Java/CORBRA based computerized patient record." in Proc. Healthcare Information Management Systems Society (HIMSS) Feb. 1999, Atlanta, GA.

* cited by examiner

Primary Examiner—Emanuel Todd Voeltz
Assistant Examiner—George D. Morgan
(74) Attorney, Agent, or Firm—Dwight H. Renfrew, Jr.

(57) ABSTRACT

This invention relates to an object-oriented system and method for easily and rapidly distributing medical images from existing picture and report storage systems to a plurality of heterogeneous client workstations. The system includes one or more interface engines, for providing image objects with uniform structure regardless of the type of existing system on which they are stored, and image server middleware, for managing the distribution of image objects. The system also includes a security object server, for authorizing user access to the image distribution system and to particular objects, a personalization object server, for providing user interface preferences and client workstation capabilities, and a web server, for downloading initial access pages and user interface components. The system implements a method for medical image distribution according to which image data stored in existing picture storage systems is first converted into a uniformly structured image objects before being composed for downloading to client workstations for user viewing. The system and method of this invention are easily extensible both for added function and for added performance. The system and method of this invention are preferably implemented according to CORBA standards.

23 Claims, 4 Drawing Sheets

COMPUTER-BASED MEDICAL IMAGE DISTRIBUTION SYSTEM AND METHOD

BACKGROUND OF THE INVENTION

1. Field of the Invention

The present invention relates to a computer system and method for enabling uniform access to and ready distribution of medical images and associated records in electronic form via a network, such as an intranet or the Internet, from multiple heterogenous and incompatible existing server systems.

2. Description of the Related Art

Handling of medical images, and of associated medical information, has been profoundly changed by the impact of digital and computer technologies. But in the current state of the art, these technologies have not resulted in uniform system by which a user can readily access medical image information from multiple and incompatible existing server systems.

Picture Archiving and Communication and Radiology Information Systems

Medical images are currently acquired by diverse imaging technologies and methods, including, for example, such methods as X-ray imaging, computed X-ray tomography, radioisotope emission imaging, computed emission tomography, magnetic resonance imaging, ultrasound imaging, and so forth. With increasing prevalence, medical images acquired by these and other methods are being directly acquired in or converted into digital form for storage and retrieval.

Current computer systems for storage and retrieval of such digital medical images (generically named Picture Archiving and Communication, or "PAC", systems), typically have large amounts of digital storage, a processor for storing and indexing images, and user workstations attached directly, or across a network, to the PAC systems for image display. These systems have usually been designed with a client-server, or two-tiered, structures. In such structures, the workstations, acting on the second-tier as image clients, run specific software designed for interacting with a specific PAC system, acting on the first tier as an image server, in order to obtain and display images. The specific server software on the PAC system is designed to accept and respond only to the specific requests from the corresponding image-clients.

Therefore, two different PAC systems having different client and server software cannot be expected to be able to exchange image data. A user needing to access multiple different PAC system needs a specific client suited for each PAC server system.

Similarly text interpreting medical image and associated patient information is being transcribed into or captured directly in digital form and stored on server systems (generically named Radiology Information, or "RI", systems). RI systems, like PAC systems, are also usually designed as client-server, or two-tiered, systems with user workstations running specific client software that interacts only with specific server software on the RI system.

Also like PAC system, two different RI systems cannot be expected to be able to exchange image data, and a user needs multiple specific clients suited for each RI server system of interest. Indeed, a PAC system is even less likely to be able to exchange data in any fashion at all with an RI system.

Other specialized information systems exist in the health-care environment. For example, there are specialized departmental-scale systems, such as those for storing and retrieving diagnostic cardiology images, for interfacing to and reporting results from laboratory instruments, for pharmacy management, and so forth. There are also institution-scale Hospital Information ("HI") systems, such as those for patient financial and billing, or for patient admissions, discharge, and transfer ("ADT").

All of these systems, like PAC and RI systems, comprise specialized software designed for the particular application and also often structured in a client-sever, two-tiered, architecture. And like PAC and RI systems, these departmental- or institution-scale information systems (e.g., HI systems) present in the health-care environment cannot be expected to exchange data or to interoperate. Users typically require a separate client to interface each of these systems.

Incompatibility Problems Associated with Current Standard Efforts

One approach to solving these incompatibilities is standardization of messages or interfaces. However, standardization alone is at best only a partial solution to solving system incompatibilities and to providing uniform data access. For example, the Digital Imaging and Communications in Medicine ("DICOM") is one standard relevant to medical image distribution. DICOM has been developed and promoted by the American College of Radiology/National Equipment Manufacturers Association (ACR/NEMA), and aims to standardize formats for exchange of image data in PAC systems by defining a standard set of basic and composite data types along with a standard set of requests involving those data types, all of which are representative of the imaging activities in a radiology department. Accordingly, a single workstation with a DICOM-conforming client can expect some success in accessing multiple PAC systems, also DICOM-conforming, and the multiple DICOM-conforming PAC systems can themselves expect some success in exchanging image data. Individual variations in the details of DICOM-conformance may defeat interoperability or data interchange.

A similar standard applicable to RI systems is HL7, a standard that aims to define formats for electronic data interchange in health-care environments, In particular, HL7 defines message formats for exchange of information relating to a broad range of health-care activities, including patient admissions, discharges, transfers, patient queries, billing, clinical observations, and orders, and eventually patient medical records generally. Because of such broad goals, HL7 is even less of a true "plug-and-play" standard than is DICOM. In other words, two systems, although conforming to HL7, are likely, nevertheless, not be able to exchange requests and data. Therefore, a single user may still require multiple clients in order to access multiple RI systems, even though they are all HL7 conforming.

Yet a further problem is due to the multiple standards, such as DICOM and HL7 in radiology, present in the health-care environment. Even if they individually achieve plug-and-play interoperability, and not all do, the various standards do not interoperate for data interchange among themselves. For example, even within one radiology department, a DICOM-conforming PAC system cannot exchange requests or data with an HL7-conforming RI system. Although, the multiple health-care data exchange standards may reduce system incompatibilities within their individual scopes, as a collection they do not achieve reduced system incompatibilities outside across their scopes as a whole within a health-care institution generally.

Therefore, the current state of the art in medical image distribution faces daunting problems due to a lack of uniform access to and interchange of medical images stored in various different PAC systems, and also to a lack of uniform access to and interchange of associated medical interpretive text information stored in RI and other health-care systems.

What is needed, therefore, is a method and system by which a user can uniformly and rapidly access medical image data without regard to the boundaries of existing PAC, RI, or other health-care systems. Further, since health-care personal often do not have fixed work locations, needing to respond to health-care problems promptly wherever they happen to be, such uniform and rapid access should allow users to access medical image information from many diverse local or remote workstations. And since patients also move, such uniform access should provide medical image information between separate health-care institutions.

SUMMARY OF THE INVENTION

It is an object of the present invention to provide a solution to the above problems of the incompatibilities of existing PAC and RI systems and of lack of uniformity of access to their stored image data. This object is achieved by novel and innovative application of computer middleware technologies to create a three-tiered information system architecture. The resulting system achieves surprising benefits, including scalability in performance and in function. Hardware can easily be added or removed to achieve necessary performance at low cost; additional processing modules can be easily added to achieve uniform access to additional image data formats, or even to additional health-care client-server systems.

The middleware software of the present invention which processes data and requests to existing PAC and RI systems into a common format and structure. Medical images and associated medical information, and indeed general patient data, can then be made uniformly available to user workstations. A single workstation can access data from a diverse range of prior-art PAC and RI systems by running single client software which need only interact with the provided common format and structure. Further, existing PAC and RI systems can efficiently exchange data through the medium of this common format and structure.

Generally, the system includes one of more interface engines, for providing image objects with uniform structure regardless of the type of existing system on which they are stored, and image server middleware, for managing the distribution of image objects. The system also includes a security object server, for authorizing user access to the image distribution system and to particular objects, a personalization object server, for providing user interface preferences and client workstation capabilities, and a web server, for downloading initial access pages and user interface components. The system implements a method for medical image distribution according to which image data stored in existing picture storage systems is first converted into a uniformly structured image objects before being composed for downloading to client workstations for user viewing. The system and method of this invention are easily extensible both for added function and for added performance. The system and method of this invention are preferably implemented according to CORBA standards.

In a first embodiment, this invention includes a medical image distribution system for distributing medical images from one or more existing storage systems to a plurality of network-attached client workstations, said medical image distribution system comprising one or more computer systems, and wherein each said network-attached client workstation is configured with an object-oriented graphical interface for receiving medical image requests from a user and for displaying medical image objects to the user; and wherein said one or more computer systems are configured with one or more interface engines, each said interface engine for retrieving medical image data from one or more existing storage systems and for presenting retrieved medical image data as medical image objects with a uniform object-oriented structure, and one or more image object coordinators for receiving medical image requests transmitted from one of said graphical interfaces, for obtaining medical image objects in said uniform object-oriented structure from said one or more interface engines, for composing said medical image objects for display by said graphical interface, and for transmitting said composed medical image objects to the requesting graphical interface.

In a first aspect, the first embodiment also includes that said one or more computer systems are further configured with one or more report interface engines for retrieving medical report data associated with said medical image data from one or more existing storage systems and for presenting retrieved medical report data as medical report objects with a uniform object-oriented structure, and wherein said one or more image object coordinators further receive medical report requests associated with said medical image data transmitted from one of said graphical interfaces, obtain medical report objects in said uniform object-oriented structure from one or more report interface engines, compose said medical report objects for display by said graphical interface, and transmit said composed medical report objects to the requesting graphical interface.

In a second aspect, the first embodiment also includes: that said one or more computer systems are further configured with a plurality of image object coordinators; that said one or more computer systems are further configured with one or more security object servers for checking the authorization of said user to access the medical image distribution system and to access requested image objects; that said one or more computer systems are further configured with one or more personalization object servers for providing to said image object coordinator information for composing said image objects according to interface preferences of the user and according to capabilities of the client workstation; that said one or more computer systems are further configured with one or more web servers for downloading access-data forms and object-oriented graphical interface modules to client workstations; and that said one or more computer systems are further configured with infrastructure modules of a distributed object system.

In a third aspect, the first embodiment also includes that said medical image data comprises radiology image data or cardiology image data.

In a fourth aspect, the first embodiment also includes: that said one or more computer systems are further configured with one or more cardiology interface engines for retrieving cardiology image data from one or more existing storage systems and for presenting retrieved cardiology image data as cardiology image objects with a uniform object-oriented structure; and said one or more computer systems are further configured with one or more cardiology image object coordinators for receiving cardiology image requests transmitted from one of said graphical interfaces, for obtaining cardiology image objects in said uniform object-oriented structure from said one or more cardiology interface engines, for composing said cardiology image objects for display by said graphical interface, and for transmitting said composed cardiology image objects to the requesting graphical interface. Further in the fourth aspect, the first embodiment also includes that the system further comprises a middleware database for storing persistent data comprising definitions of said uniform object-oriented structures of said cardiology image objects.

In a fifth aspect, the first embodiment also includes that the system further comprising a middleware database for storing persistent data and objects and wherein said middleware database stores definitions of said uniform object-oriented structures of said medical image objects.

In a sixth aspect, the first embodiment also includes that said one or more computer systems are further configured with one or more additional interface engines, for presenting additional medical data retrieved from existing systems as additional medical data objects with a uniform object-oriented structure, and one or more additional object coordinators, for coordinating transmission of additional medical data objects to requesting graphical interfaces; and wherein said additional medical data comprises pharmacy data or medical laboratory data.

In a second embodiment the invention includes a method for medical image distribution from one or more existing image storage systems to a user at a client workstation comprising: obtaining a user request for a medical image; obtaining image data for the requested medical image from one of said existing image storage systems; converting said image data into one or more image objects having a uniform object-oriented structure; composing said one or more image-object according to user preferences and client workstation capabilities; and displaying said composed one or more image objects to the user.

In a first aspect, the second embodiment also includes, prior to the step of obtaining image data, steps of checking identification provided by the user to authorize the user to obtain medical images and of checking the authorization of the user to access the requested medical image object.

In a second aspect, the second embodiment also includes, prior to the step of obtaining image data, a step of accessing a master patient index for patient identification.

In a third aspect, the second embodiment also includes, prior to the step of obtaining a user request, a step of downloading graphical interface modules to the client workstation.

BRIEF DESCRIPTION OF THE DRAWING

Other objects, features and advantages of the present invention will become apparent upon perusal of the following detailed description when taken in conjunction with the appended drawing, wherein.

DETAILED DESCRIPTION OF THE PREFERRED EMBODIMENTS

Figure 1:
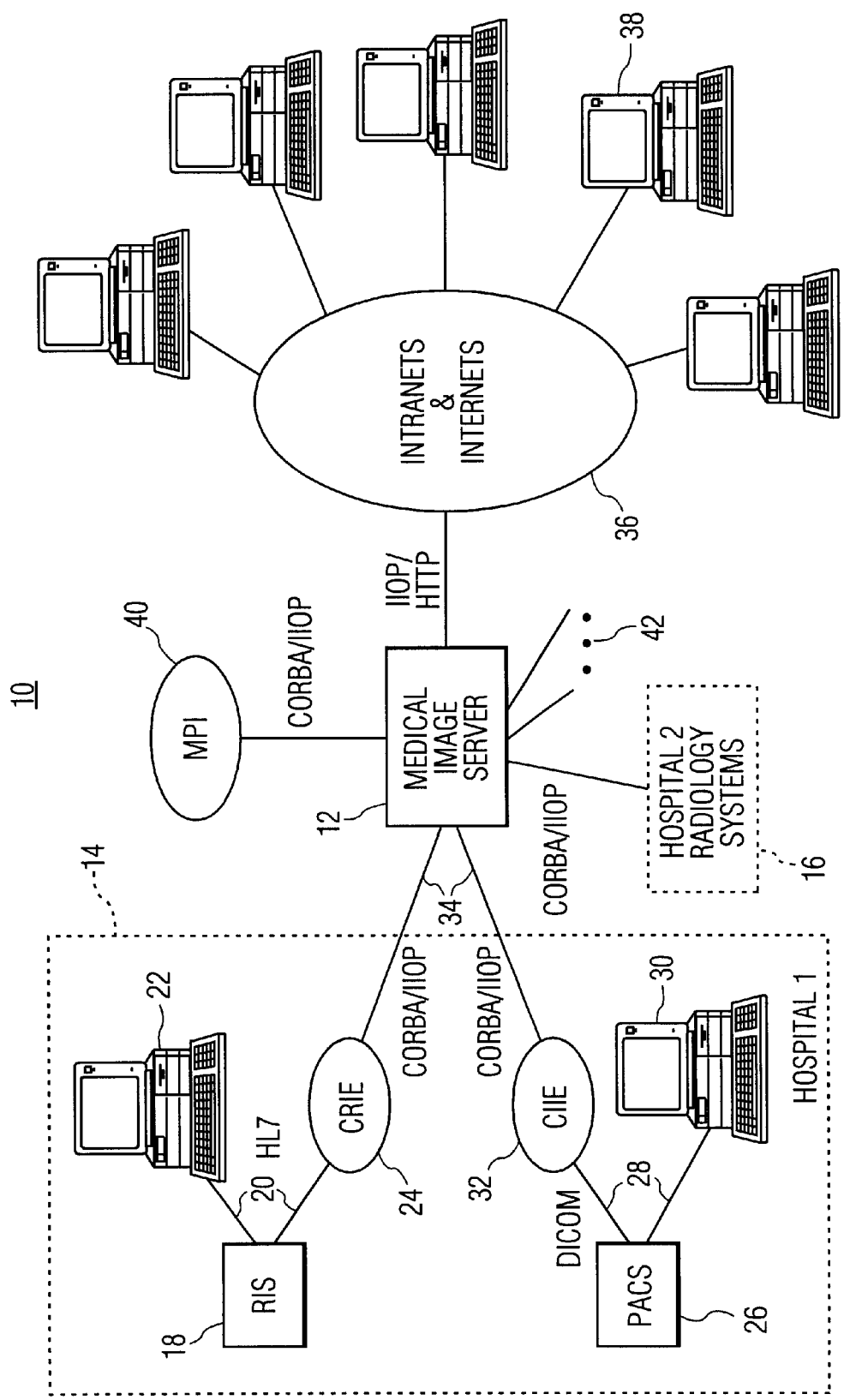
FIG. 1 illustrates an embodiment of a computer system in accordance with the present invention.

The medical image server middleware is built upon a distributed object infrastructure, which is described next. In view of the capabilities of this infrastructure, hardware and software architectures of the middleware are described following. Finally, details of the middleware databases and request processing procedure are described.

Distributed Object Infrastructure

The middleware software for medical image distribution according to the present invention is structured according principles of distributed object-oriented programming. Object-oriented programming, generally, as is well-known to those of skill in the art, structures programs into objects, each of which is a self-contained collection of data and of methods which act on the data. Program execution occurs as client objects make requests of and receiving data from server objects.

Distributed object-oriented programming includes infrastructure permitting, inter alia, client objects and server objects to reside, indiscriminately and transparently, on one computer or on different computers, even different heterogenous computers. Preferably, there can be more than one server capable of responding to a particular client request with the ORB responsible for selecting which server is to respond to each particular client request. This infrastructure typically included an object request broker ("ORB") component, which is present on the different computers and is responsible for transparently managing, locating, and communicating between client and server objects.

This invention is equally adaptable to the various commercially available distributed object-oriented computing infrastructures. Such infrastructures are preferred if they conform to the CORBA family of standards of the Object Management Group, Inc. ("OMG") (Newton, Mass.; and http://www.omg.org). Such commercial infrastructures are available from, inter alia, Borland, Inc. (Scotts Valley, Calif.) and from IONA Technologies, Ltd. (Dublin, Ireland). Where all computing systems run one of the Windows™ operating systems from Microsoft Corp., this invention is also adaptable to the Component Object Model from that vendor.

A distributed object infrastructure conforming to CORBA includes at least both an Interface Definition Language ("IDL") omplementation and an ORB. The IDL is a uniform, declarative language for defining all object interfaces in the middleware. The ORB is responsible for activating one or more instances of server objects, routing requests and responses between client objects and server objects, transparently managing all communication details of request routing, providing for object persistence and for object replication for reliatility or performance. The ORBs resident on the various computers forming a system according to this invention preferably communicate among themselves for request routing according to the Internet Interorb Protocol ("IIOP"), which is an implementation of the generalized interorb protocol using the TCP/IP communications protocol suite widely available on, for example, the Internet and private intranets. A preferred CORBA implementation includes relevant object servers defined by CORBA Common Services and Common Facilities standards. Implementations of IDL-defined object interfaces are preferably coded in C, C++, or Java®.

Although the following description of the preferred embodiment conforms to the CORBA family of distributed object standards, it will be readily apparent to one of skill in the art that equivalent embodiments of this invention conform to other equivalent distributed object standards.

The hardware and software architectures described in the following sections can be readily understood in view of the preceding description of distributed object systems.

Medical Image Server Hardware Architecture

Referring now to FIG. 1, there is shown exemplary embodiment 10 of a medical image distribution system according to the present invention. The basic three-tier architecture of this system is apparent from this figure. In the first tier are existing medical image information systems, represented generally as system 14 at Hospital 1, system 16 at Hospital 2, and so forth, which currently store medical images and associated information. Also in the first tier, represented schematically at 42, are additional existing systems which can store non-radiology, e.g., cardiology, related medical images or other medical information other than images made uniformaly and rapidly available through the medical image server of this invention. In the second tier is medical information server 12, which provides for uniform and rapid distribution of information between the first-tier systems and the third-tier client systems, such as workstation 38. Although illustrated as a single system, as well become apparent subsequently, medical image information server 12 can be implemented either on more than one computer system, according to convenience and performance requirements, or can be collocated on one computer system with other components of the image distribution system of this invention. Also present in the middle-tier are other object-based health-care information systems, in particular Master Patient Index ("MPI") system 40. Third-tier client systems include user equipment ranging from thin clients, to standard PCs, to more powerful UNIX workstations, as well as possibly including specialized devices All such client devices are referred to herein as "client workstations or simple as "workstations".

In more detail, an exemplary existing medical image information system, such as might currently be found in a hospital and interfaced to middle-tier medical image server 12 of the present invention, is represented by equipment 14. Illustrated therein are an existing PAC system 26 which communicates to attached systems over links 28, perhaps conforming to a version of the DICOM standard. The attached systems include workstations, such as workstation 30, dedicated to PAC image display functions.

Also attached is CORBA Image Interface Engine ("CIIE") 32, which interfaces between the PAC system and medical image server 12. Interface engine 32 functions as a server of image objects with IDL defined interfaces, which are the uniform for all attached PAC systems. Upon receipt of a client image object request transferred, for example, according to the CORBA/IIOP protocol, the CIIE implementation translates it into an equivalent PAC system request, perhaps formatted in a DICOM compliant manner. Upon receipt of the PAC image data or response, the CIIE implementation formats it according to the defined IDL interface into a response to the client object, which is transmitted according to the CORBA/IIOP protocol over links 34. In this manner, the specialized details of the PAC system are hidden from a client, which sees only uniform image object interfaces accessible by standard CORBA/IIOP protocols regardless of the details of the PAC system, such as whether it is DICOM compliant or not. The CIIE maps the IIOP protocol onto the DICOM conformant interfaces, or other proprietary interfaces, of the PAC system.

Also present as part of the exemplary medical image system is RI system 18. This system also communicates over links 20 to attached workstations, such as workstation 22, in a manner which is optionally be HL7 compliant. Also attached to RI system 18 is CORBA Report Interface Engine ("CRIE") 24, which performs a similar function for the RI system as CIIE 32 performs for the PAC system. In particular, CRIE interface engine 24 functions as a interface for report objects with IDL defined interfaces, which are uniform for all attached PAC systems, and which are accessible according to the standard CORBA/IIOP protocol. Accordingly, the specialized details of the RI system are hidden from a client object, which sees only uniform report object interfaces regardless of the details of the RI system, such as whether it is HL7 compliant or not. In detail, upon receipt of a client report object request transferred according to the CORBA/IIOP protocol, the appropriate CRIE implementation translates it into an equivalent RI system request, perhaps formatted in a HL7 compliant manner, and upon receipt of the RI report data or response, the CRIE implementation formats it according to the defined IDL interfaces into a response to the client object, which is transmitted according to the CORBA/IIOP protocol over links 34.

CRIE 24 and CIIE 32 are illustrated for purposes of illustration and without limitation as separate systems collocated in Hospital 1 with the interface PAC and RI systems. Alternatively, these interface engines may reside on a single system, which can be optionally collocated with medical image server 12. Also for purposes of illustration, these interface engines are illustrated as each interfacing one PAC or RI system. Alternatively, each interface engine can interface more than one PAC or RI system of the same type, separate interface engines generally being required to interface to different types PAC or RI systems in order to match each system's unique interface definition to the uniform object interfaces defined in the medical image server of this invention. The instant invention includes the other implementation details that will be apparent to one of skill in the art.

Returning to FIG. 1, the remaining components of the exemplary system therein illustrated are now described in more detail. Master Patient Index ("MPI") system, is a middle-tier system, preferably present in order to obtain relevant patient identifiers for use in the system of the present invention. Each existing first-tier PAC and RI system typically implements patient identifiers which are unique and specific to that system. Medical image server 12 may implement and require another form of patient identifiers. Finally, health-care personal using the medical image server system usually easily identify patients in terms of name along with certain demographic characteristics instead of with details of the patient identifiers maintained by the various systems having patient information of interest. MPI system 40 is an object-based middleware server present in a system of this invention to translate between these forms of patient identification. Although this invention is adaptable to any MPI system providing such function, in a preferred embodiment, MPI system 40 implements interfaces defined by the OMG/CORBAmed Patient Identification Services ("PIDS") and Master Patient Index IDL standard (available from the OMG).

In the third-tier of the medical image distribution system of this invention are client systems, such as system 38, presenting graphical user interfaces ("GUI") which health-care personal use to request and view medical image information from the medical image distribution system. Client systems are linked via network links 36 to medical image server 12. Preferably, links 36 implement the TCP/IP suite of protocols, and accordingly, can be a campus intranet, a wide-area intranet, or even the Internet. In each situation, appropriate security protocols, for example the secured socket layer or other link encryption protocols, are used to insure confidentiality of medical information.

In a preferred embodiment, the client GUI is implemented as an object-oriented interface components of which are downloaded as needed from image server 12. Since only Java currently provides for such download, the client GUI is preferably written either as a Java application or as Java applets in conjunction with a web-browser. The GUI interface present client objects that request information, in particular, medical image data, from medical image server 12. Advantageously, therefore, client and server objects communicate, mediated by the ORBs, over network links 36 using the CORBA/IIOP protocol. In the preferred embodiment, the Java application or applets can be downloaded dynamically when a health-care user accesses the image distribution system and requests particular image data. In that manner, the GUI appropriate for the particular user, the particular workstation, and the particular image data can be made available at any user access equipment. Since the GUI components necessary for particular information or images are downloaded with the images, the most appropriate image display can always be assured throughout the system. A further advantage of the latter arrangement is that display of new types of information can be automatically and routinely provided for by simply downloading new Java-coded GUI objects for their display.

Where all GUI components are dynamically downloaded, the workstation equipment can be a "thin client" with minimal attached resources, perhaps only a Java virtual machine. Alternately, where the network links to a particular workstation have low bandwidth, certain base GUI components can be cached on the workstation. In a further alternative, the entire GUI can be present on the workstation and coded in another object-oriented language, such as C++.

Medical Image Server Middleware Software Architecture

Figure 2:
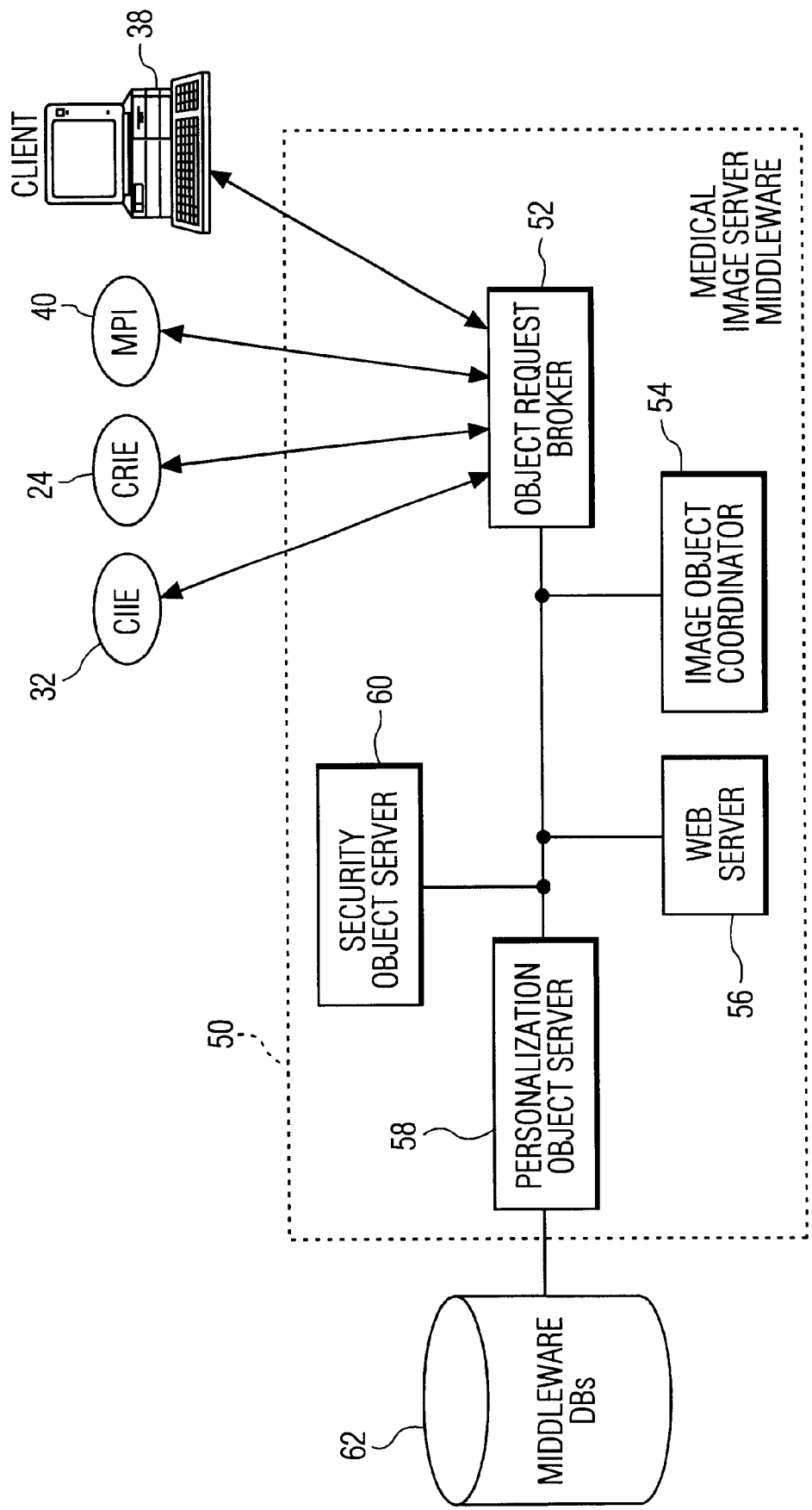
FIG. 2 illustrates an embodiment of a software architecture for the middleware of the present invention.

FIG. 2 illustrates the detailed software architecture of an exemplary preferred embodiment of the principal components of the image server middleware 50 for medical image server 12. Each illustrated component is individually described in the following. First, Object Request Broker ("ORB") 52 plays a key system role in enabling the other objects of the system to make requests and receive responses in a distributed environment. One ORB is present on each computing system hosting the image server middleware. The ORB routes invocations between client and server objects transparently, so that these objects do not need to be aware of any communication details or network structure. Where objects reside on the same machine, requests and responses are routed preferably by direct procedure calls internal to the resident machine between the objects and the ORB. Where objects reside on different computing machines, the ORBS on the two machines communicate the requests and responses between the objects via the CORBA/IIOP. The ORB also assumes responsibility for object management, including, for example, object activation and termination, object replication, object persistence, and so forth.

The client and server objects may be part of the image server middleware itself or may reside on other tiers of the system. Thus, ORB 52 participates in routing requests from objects in client workstations 38 to various middleware object servers, principally image object coordinator 54. It also participates in routing requests to the interface engines, CIIE 32 and CRIE 24, which provide object implementations of the first-tier PAC and RI systems.

ORB services permit the image server middleware to have easily scalable performance. When any particular object server, for example image object coordinator 54, becomes too highly utilized, an additional instance of the server can be activated by the system ORBs and service requests divided between the object servers. More than two instances can be created if necessary. Similarly, when any particular computer system hosting the image server middleware becomes too highly utilized, additional object server instances can be activated on less heavily utilized computer systems. Conversely, when utilization falls, object server instances can be terminated. Dynamic routing of requests and responses between client and server objects on the various computer systems is performed automatically by cooperation among the system ORBS on the various machines.

Before describing image object coordinator 54, which is central to the operation of the image server middleware, supporting personalization object server 58 and security object server 60 are described. The personalization object server is a CORBA object server that stores and retrieves profile data from the middleware database. The profile data can include client system profile data and user profile data. Client system profile data defines the characteristics of a particular client workstation currently accessed by a user, including, inter alia, hardware characteristics such as display resolution and network link speed, and software characteristics such as whether the GUI is resident or to be downloaded. User profile defines user adjustable GUI preferences, such as display layout preferences, font sizes, and default medical image resolutions.

The security object server provides security and access control information necessary to protect medical image data from unauthorized access. Security information specifies, inter alia, key management and encryption algorithms to be used in user sessions with particular client workstations over particular network links. Access control information includes, inter alia, user access control and object access control information. User access control identifies and legitimizes a particular user of the system, and can be by traditional user-id and password or by newer biometric techniques, such as fingerprint identification. As part of legitimization, this information can also specify user role and group, for example, attending or resident physician, nurse and so forth, and object access privileges, for example, all patients, all assigned patients, limited data for assigned patients, and so forth. Object access control information can specify, for each object or group of objects, which users or user groups are allowed access and what levels. Optionally, the security object server can also provide services to date and log an audit trail of each user session.

Again referring to FIG. 2, image object coordinator 54 plays a central role in the image server middleware. Generally, this object server receives client object requests generated by the GUI from user input transparently via ORB 52 from the object-oriented GUI running on a client workstation, such as workstation 38, accessed by the user for medical image data or report data. This object server then, first, checks that the user is authorized to access the requested data by comparing user and object access information from the security object server. If access verification fails, an indication of this failure is returned to the client. Second, if the access verification succeeds, this server interprets these requests and forwards them, again transparently via ORB 52, to the appropriate object interfaces presented by the appropriate CIIE and/or CRIE. Next, responses from the first-tier systems are retrieved from the CIIE and/or the CRIE object interfaces, and the image object coordinator composes the responses for transmission to the client workstation according to the user profile preferences and the client workstation capabilities obtained from the personalization object server. Finally, the image object coordinator returns the composed responses to the object-oriented GUI completing a response to the user request.

As described above, CIIE 32 and CRIE 24 are interface engines which present an object-oriented interface to existing first-tier PAC and RI systems. Accordingly, their object implementations receive and respond to client object requests, principally from the image object coordinator, using CORBA/IIOP protocols between the system ORBs in the middleware server computer systems. The interface engines communicate with the existing systems in their own, perhaps proprietary, message or command formats. However, for PAC systems, communication is preferably conformant to the DICOM standard, and for RI systems, the HL7 standard. There may be one or more of each of the interface engines in an image server system.

The interface engines together with the image object coordinator present medical image object and report object interfaces to client objects that are uniformly defined regardless of the types of the interfaced PAC and RI system. These object interfaces are designed to provide the basic image, patient, and interpretation information known in the art. One or more versions of these uniform object interfaces may be available depending on image or report type. The structure of these interfaces is preferably made available as object definitions in middleware database 62. Accordingly, the GUI interfaces at client workstations can query this database and determine the structure of available image objects.

Concerning image information, the object interfaces provide basic medical image characteristics and image data for radiography images, computed tomography image, magnetic resonance images, nuclear medicine images, ultrasound images, and so forth. Image information is identified as single frame images, groups of single frame images, multi-frame images, and so forth. Concerning patient information, the object interfaces provide for patient identification and demographic information, patient visit information, patient study information, study component information, for the relation of image and patient information, and so forth. Concerning interpretation information, the object interfaces provide for results and interpretation information and for the relation of interpretation information to the other classes of information. Although, the object interfaces are described without limitation in terms of known imaging modalities and techniques, these interfaces can be extended to accommodate provide for new imaging modalities and techniques.

Preferably the object interfaces are defined in CORBA/IDL. Even more preferably, the IDL definitions conform to present or future image and report object standards. Such standards are being defined by, inter alia, the OMG, in particular by its CORBAmed task forces.

The remaining elements of the middleware software architecture are MPI (master patient index) 40 and web server 56. As described above, the MPI is a, preferably CORBAmed standardized, object server that provides unique patient identification needed for accessing existing first-tier systems. When image object coordinator 54 is presented with a user request for image or report data for an identified patient, it may optionally need to access MPI 40 to translate the patient identification provided by the user into unique patient identification understandable by attached PAC or RI systems.

In addition to the MPI, other object-oriented medical information systems can be directly linked with the image-server middleware. If such object-oriented system communicate with common protocols, for example the CORBA/IIOP protocol, they can be immediately linked and their information made immediately available. If common protocols are not available, a thin protocol wrapper may be necessary to provide for communication.

Finally, web server 56 provides infrastructure, non-object-oriented functions necessary for initiating and maintaining user sessions. At session initiation, web server 56 downloads access information. Where the client workstation accesses the system through a web browser, this information preferably includes HTML (hypertext transfer markup language) or XML (extensible markup language) pages defining system logon. After a session is started, this sever downloads GUI components as needed for the medical image and report information to be displayed. These typically include Java applets for a web browser or a complete Java GUI application. Alternatively, where part of the GUI are cached or resident on a client workstation, web browser 56 may need only to provide for session initiation.

All object servers, object coordinators or interface engines of the image server middleware 8 are preferably CORBA object servers implemented with defined Interface Definition Language interfaces. They communicate with each other either through the collocated ORB, if the object reside in the same machine, or through multiple system ORBs using the IIOP protocol, if they reside across different machines on the Internet. All other properties pertinent to CORBA object servers apply to these object servers.

In particular, although this invention is described as if the image server middleware included only one object server, object coordinator, or interface engine of each type, in fact this middleware can include more than one entity of each of these types. The object servers or interface engines can be replicated on the same or on different machines. Such object server, object coordinator, or interface engine replication provides for performance scalability, as described elsewhere herein.

Importantly, it also provides for fault tolerance in the highly mission-critical nature of medical care computer systems. Each type of object server, object coordinator, or interface engine can have one or more backup servers or engines of that type present in the systems. In case of a failure of a primary object server or interface engine, requests can be immediately switched to the backup server or engine, using ORB facilities, so that the system will appear to function without interruption. The backup servers can, optionally, be idle in the absence of a primary failure. Analogously, computer and communication systems can be replicated with object servers, object coordinators, or interface engines of each type present in each of the replicated systems. Upon failure of a computer system or communication link, the ORB infrastructure can immediately route requests to servers or engines on functioning systems or links, again maintaining overall system availability with interruption. Further options for providing fault-tolerance using this architecture will be apparent to those of skill in the art.

In addition to CORBA, this invention is adaptable to other distributed object standards and implementations with similar functions. These alternatives include the Component Object Model of the Microsoft Corp.

Middleware Database Structure

Figure 3:
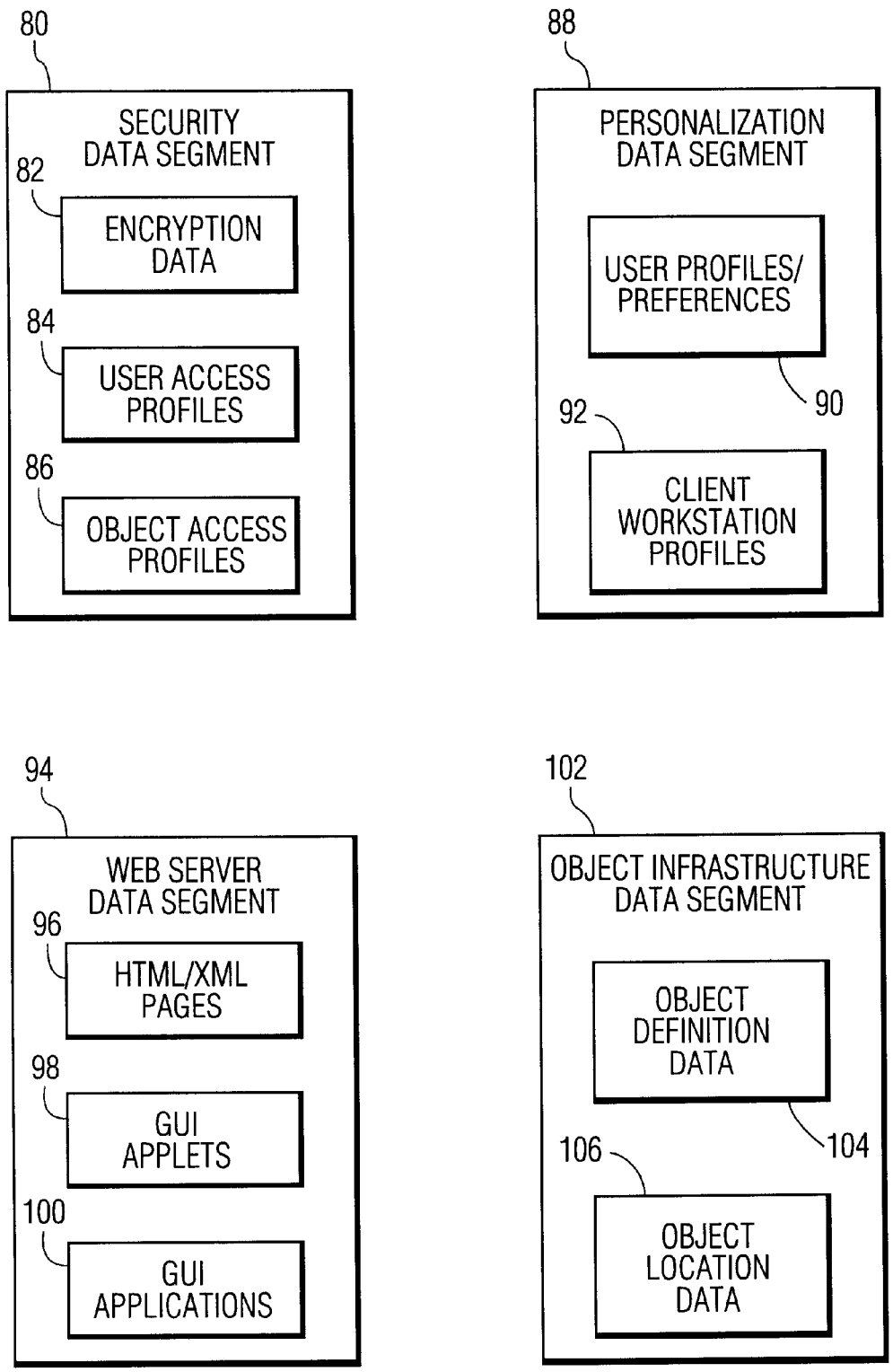
FIG. 3 illustrates an embodiment of the middleware database in accordance with the present invention.

The middleware database, reference number 62 in FIG. 2, stores data and persistent objects necessary for the functioning of the image server middleware. Database 62 can be implemented in a single storage device or in a combination of such devices. In an exemplary preferred embodiment, this middleware database can be structured, as illustrated in FIG. 3, into segments particular to each of software architectural elements of the image server illustrated in FIG. 2. These are segments are individually described below.

Security data segment 80 includes encryption component 82, which stores link and session security data, such as encryption algorithms uses, key management protocol directions, and so forth. User access component 84 stores user authorization data, such as access information, for example, userid/password, biometric signatures, or so forth, user role, user access group membership, and so forth. Optional object access profile component 86 stores object access information, such as the user groups, user roles, and so forth which are allowed access to particular objects or groups of objects. Accordingly, the security object server using the encryption component can establish appropriate link and session security to prevent eavesdropping. Using the user access profile component it can authorize a user to access the system, and along with the object access component, it can allow access only to authorized objects. This segment is preferably structured as an object-oriented database.

Personalization data segment 88 includes user profiles/preferences component 90, which stores user GUI preferences, and optional client workstation component 92, which stores workstation characteristics. Accordingly, the personalization object server, using both components, provides that any user can access the medical image distribution system of this invention at any workstation and receive image and data presentation according to the user's preferences and within the capabilities of the workstation that the user happens to access. This segment is also preferably structured as an object-oriented database.

Web server data segment 94 primarily includes data needed for download to client workstations. This data includes initial presentation information stored in HTML/XML page component 96. The web server also downloads appropriate components of the GUI as needed for entry of users requests and for display of image data. These GUI components are preferably structured as Java applets for workstations hosting a web-browser or, alternatively, as a complete Java GUI applications, and are stored in GUI applets component 98 or in GUI application component 100, respectively.

Finally, the object infrastructure, in particular the system ORBs, requires certain data, optionally depending on the particular distributed object implementation, in order to carry out request routing and object management. This data is stored in object infrastructure segment 102, and is generally represented as object definition data component 104 (also known as an object definition repository) and in location data component 106. The object definition component stores data defining the object interfaces between which the system ORBs must route requests, in particular, definitions of the structures of available image and report objects are stored here. The location data component stores object identifiers and other data defining current physical location and message routing information for performing CORBA/IIOP communications.

This invention is equally adaptable to alternative database structures for middleware database 62 (of FIG. 2) data that contain equivalent data and that will be apparent to those of skill in the art.

General Request Processing Procedures

Figure 4:
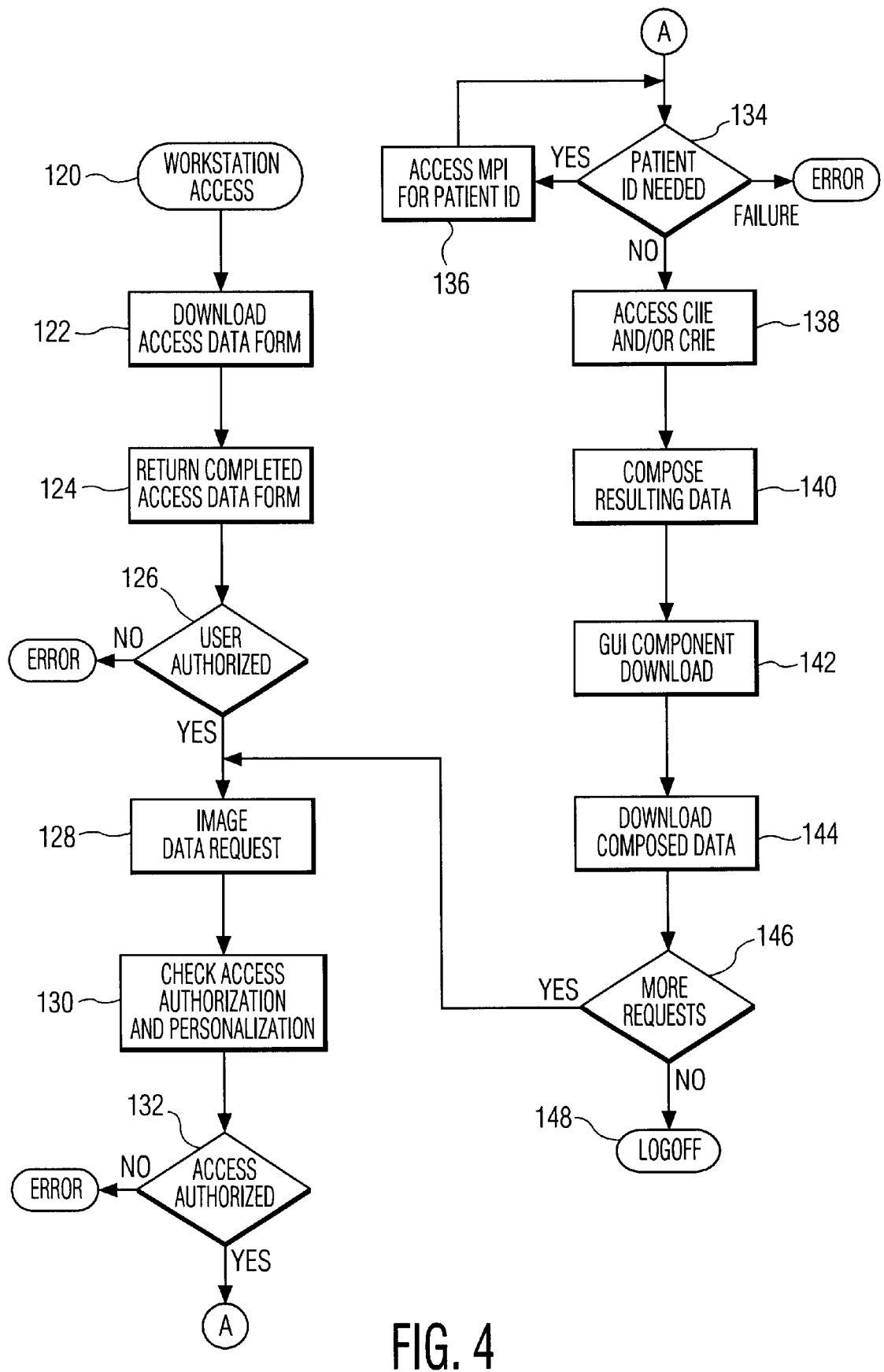
FIG. 4 illustrates an embodiment of user request processing in accordance with the present invention.

A general preferred exemplary procedure for processing user requests for medical image or report data is described in this section with reference to steps illustrated in FIG. 4.

Beginning at step 120, a user physically access a client workstation, and at step 122 requests download of an access-data form by the web server. For example, an HTML home-page of the medical image server is downloaded by the web server into a web browser when the user enters the web address (universal resource locator) of the image server. This page requests entry of user identification information. At step 124, the user enters text or biometric identification data and the filled-in access-data form is returned from the web browser for user validation. The web server in cooperation with the security object server performs the user validation. At step 126, if the user is validated, the web server then downloads the initial Java applets or initial Java application modules to build the GUI for medical image or report requests. Also downloaded is an object reference of the image object coordinator. If the user is not validated, an error indication is returned to the client workstation.

Communication between image server middleware, in particular the web server, and client workstation in steps 120–126 preferably employs the hypertext transfer protocol ("HTTP"), or more the preferably HTTP with the secured socket layer ("SSL"), a well-known encryption protocol for securing HTTP communications.

At step 128, the user enters an image data request through the object-oriented client GUI. Using the downloaded object reference of the image object coordinator, this request is interpreted into method calls to the image object coordinator to retrieve and download the desired image. The image object coordinator upon receiving an image request, first, at step 130, in cooperation with the security object server, checks whether this user is authorized to access the desired object. At step 132, if authorization is denied, an error indication is returned to the client workstation.

Otherwise, at step 134, the image object coordinator checks the user-supplied patient identification for adequacy. If it is inadequate, the MPI is consulted at step 136 in order to attempt to determine adequate patient identification for the first-tier PAC or RI systems storing the desired image data. If adequate patient identification is not determined after one or more attempts, perhaps including requests to the user for additional patient information, then an error indication is returned to the client workstation at step 134.

If adequate patient identification is determined, then at step 138 the image object coordinator accesses the object interfaces of the appropriate CIIE or CRIE. These interface engines, in turn, request and retrieve the desired image or report data from the existing first-tier systems using these systems existing protocols.

At step 140, the image object coordinator composes the returned image data into formats and resolutions defined by the personalization object server for this particular user and this particular client workstation.

At step 142, the web server can be called, if necessary, to download GUI components, for example, Java applets, that are necessary to display this particular type of image or data on this particular type of client workstation. Finally, at step 144, the composed requested data is downloaded for user viewing.

Communication between image server middleware and client workstation in steps 128–144 preferably employs the CORBA/IIOP protocol for communication between distributed objects. These communications can be suitably encrypted.

Finally, at step 146 the user can either request more medical image and report data or can indicate a desire to logoff from the system. In the latter case, at step 148 the web server terminates the connection with the client workstation.

System Extensions

Although the above description has been in terms of radiology images and report data stored on existing PAC and RI systems, the medical image server according to this invention is not limited to just radiology data. One of skill in the art will readily understand how to incorporate other medical image sources and other medical data in general. It will be appreciated that the medical image system of this invention is functionally extendible by a routine procedure. It has previously been described how this system of scalable to achieve adequate performance with appropriate cost.

For example, cardiology-image data can readily be incorporated in the following routine manner which is easily performed by one of skill in view of the preceding description. Cardiology-image data can include single images or multi-image sequences useful to ascertain the functioning and adequacy of the cardiac vasculature and cardiac muscle. First, interface engines for cardiology-image data and associated report data are defined to provide object interfaces to protocols for existing cardiology data storage and communication systems. The cardiology-image transfer standard is, in fact, a variant of the DICOM standard applicable to radiology images.

Second, the image object coordinator is extended with implementation code to access the new interface engines and to compose cardiology images and reports for transmission to client workstations. The image coordinator makes available its cardiology object definitions, as well as the radiology object definitions, in the object definition data component of the object infrastructure segment of the middleware database so that client workstations can query cardiology-image related information. Alternately, the image distribution middleware can be extended with a separate cardiology-image data object coordinator that provides object coordinator functions similar to the existing image object coordinator, which thereby remains directed to radiology-image data.

Finally, if new Java applets or Java applications are needed to display cardiology image and report information, they are added to the appropriate component of the web server data store.

One of skill will also appreciate how the medical image server of this invention can be further extended to make available additional medical non-image information. The medical image distribution system would be extended, at least, with additional interface engines, for making available in a uniform object-oriented fashion the additional medical data stored in existing system, and with additional object coordinators, for retrieving and transmitting the additional uniform medical objects to client workstations. The additional medical information can include, for example, information from laboratory computing systems or from pharmacy computing systems or from administrative computing systems.

It should now be appreciated that the objects of the present invention are satisfied. While the present invention has been described in particular detail, it should also be appreciated that numerous modifications are possible within the intended spirit and scope of the invention.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A medical image distribution system for distributing medical images from one or more storage systems for medical images to a plurality of network-attached client workstations, said medical image distribution system comprising one or more network-attached computer systems, and wherein each said network-attached client workstation is configured with a graphical interface for receiving medical image requests from a user, for transmitting the received medical image requests in an object-oriented format, and for displaying medical image objects received in response to the transmitted requests to the user; and wherein said one or more network-attached computer systems are configured with infrastructure modules of a distributed object system for forwarding and transmitting of object requests and responses, one or more interface engines, each said interface engine presenting a uniform object-oriented interface for retrieving medical image data from the existing storage systems by translating requests between the uniform object-oriented format and individual formats recognized by the storage systems and for returning retrieved medical image data as medical image objects in the uniform object-oriented structure, and one or more image object coordinators for receiving the object-oriented medical image user requests transmitted from said client workstations, for obtaining objects with requested medical images by forwarding retrieval requests in the uniform object-oriented format to said one or more interface engines, for composing said obtained medical image objects according to preferences of the user and capabilities of the client workstation for display at the client workstations, and for transmitting said composed medical image objects to the requesting client workstation as a response to the transmitted object-oriented user requests.

2. The system as claimed in claim 1, wherein said one or more computer systems are further configured with one or more report interface engines, each said report interface engine presenting a uniform object-oriented interface for retrieving medical report data associated with said medical image data from the existing storage systems by translating requests between the uniform object-oriented format and individual formats recognized by the storage systems and for returning retrieved medical report data as medical report objects in the uniform object-oriented structure, and wherein said one or more image object coordinators further receive object-oriented medical report user requests associated with said medical image data transmitted from the client workstations, obtain objects with requested medical reports by forwarding retrieval requests in the uniform object-oriented format to said one or more report interface engines, compose said obtained medical report objects according to preferences of the user and capabilities of the client workstation for display at the client workstations, and transmit said composed medical report objects to the requesting client workstation as a response to transmitted object-oriented user requests.

3. The system as claimed in claim 1, wherein said one or more computer systems are further configured with a plurality of image object coordinators.

4. The system as claimed in claim 1, wherein said one or more computer systems are further configured with one or more security object servers and, wherein the security object servers, in response to object-oriented requests from the image object coordinators, check authorization of said user to access the medical image distribution system and to access requested image objects.

5. The system as claimed in claim 1, wherein said one or more computer systems are further configured with one or more personalization object servers for providing to said image object coordinators information for composing said image objects according to interface preferences of the user and according to capabilities of the client workstation.

6. The system as claimed in claim 1, wherein said one or more computer systems are further configured with one or more web servers for downloading access-data forms and object-oriented graphical interface modules to client workstations.

7. The system as claimed in claim 1, wherein said medical image data comprises radiology image data.

8. The system as claimed in claim 1, wherein said medical image data comprises cardiology image data.

9. The system as claimed in claim 8, wherein said one or more computer systems are further configured with one or more cardiology interface engines, each said cardiology interface engine presenting a uniform object-oriented interface for retrieving cardiology image data from the existing storage systems by translating requests between the uniform object-oriented format and individual formats recognized by the storage systems and for returning retrieved cardiology image data as cardiology image objects in the uniform object-oriented structure.

10. The system as claimed in claim 9, wherein said one or more computer systems are further configured with one or more cardiology image object coordinators for receiving object-oriented cardiology image user requests transmitted from said client workstations, for obtaining objects with requested cardiology images by forwarding retrieval requests in the uniform object-oriented format to said one or more cardiology interface engines, for composing said obtained cardiology image objects according to preferences of the user and capabilities of the client workstation for display at the client workstations, and for transmitting said composed cardiology image objects to the requesting client workstation as a response to transmitted object-oriented user requests.

11. The system as claimed in claim 9 further comprising a middleware database for storing persistent data comprising definitions of said uniform object-oriented formats of said cardiology image objects.

12. The system as claimed in claim 1, further comprising a middleware database for storing persistent data and objects.

13. The system as claimed in claim 12 wherein said middleware database data further comprises definitions of said uniform object-oriented formats of said medical image objects.

14. The system of claim 12 wherein said middleware database data further comprises user preferences and client workstation capabilities.

15. The system as claimed in claim 1, wherein said one or more computer systems are further configured with one or more additional interface engines for presenting a uniform object-oriented interface for retrieving additional medical data from the existing storage systems as additional medical data objects, and one or more additional object coordinators for coordinating transmission of additional medical data objects to requesting graphical interfaces.

16. The system as claimed in claim 15, wherein said additional medical data comprises pharmacy data or medical laboratory data.

17. The system of claim 1 wherein the uniform object-oriented format and the distributed object system are described by the CORBA standard.

18. The system of claim 1 wherein the individual formats recognized by the storage system comprises a format described by the DICOM standard.

19. The system of claim 1 wherein said one or more computer systems are further configured with one or more master patient index object servers, and wherein the master patient index object servers in response to object-oriented requests from the image object coordinators provide patient identification.

20. A method for medical image distribution by one or more network-attached computer systems from one or more storage systems for medical images to a user at a network-attached client workstation comprising:

receiving a user request at a client workstation for a medical image, transmitting the received user request for the medical image in an object-oriented format from the client workstation to an image object coordinator at the one or more network-attached computer systems, forwarding a retrieval request for the requested medical image in a uniform object-oriented format from the image object coordinator to an interface engine at the one or more network-attached computer systems, retrieving the requested medical image data for the requested medical image by the interface engine from one of said existing storage systems, wherein the retrieving further comprises translating requests between the uniform object-oriented format and individual formats recognized by the storage systems, composing medical image objects received by the image object coordinator from the interface engine in the uniform object-oriented format according to preferences of the user and capabilities of the client workstation, transmitting said composed medical image object by the image object coordinator to the client workstation as a response to the transmitted object-oriented user request, and displaying by the client workstation of said transmitted composed medical image objects to the user.

21. The method of claim 20 further comprising, prior to the step of forwarding a retrieval request, a step of requesting a security object server to check identification provided by the user to authorize the user to obtain medical images and of checking the authorization of the user to access the requested medical image object.

22. The method of claim 20 further comprising, prior to the step of forwarding a retrieval request, a step of requesting a master patient index object server to obtain patient identification.

23. The method of claim 20 further comprising, prior to the step of receiving a user request, a step of downloading object-oriented graphical interface modules to the client workstation.

\* \* \* \* \*